United States Patent
Tian et al.

(10) Patent No.: US 12,232,904 B2
(45) Date of Patent: Feb. 25, 2025

(54) C-ARM X-RAY DEVICE

(71) Applicant: BOE Technology Group Co., Ltd., Beijing (CN)

(72) Inventors: Chunlei Tian, Beijing (CN); Xianglei Zhang, Beijing (CN); Bingyi Yao, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 232 days.

(21) Appl. No.: 17/781,171

(22) PCT Filed: Jan. 28, 2021

(86) PCT No.: PCT/CN2021/074140
§ 371 (c)(1),
(2) Date: May 31, 2022

(87) PCT Pub. No.: WO2021/164517
PCT Pub. Date: Aug. 26, 2021

(65) Prior Publication Data
US 2023/0000457 A1    Jan. 5, 2023

(30) Foreign Application Priority Data
Feb. 17, 2020  (CN) .......................... 202010097620.7

(51) Int. Cl.
*A61B 6/00* (2024.01)
(52) U.S. Cl.
CPC ............ *A61B 6/547* (2013.01); *A61B 6/4441* (2013.01); *A61B 6/447* (2013.01); *A61B 6/4476* (2013.01)

(58) Field of Classification Search
CPC ..... A61B 6/4476; A61B 6/4405; A61B 6/547; A61B 6/4441; A61B 6/447; A61B 6/10;
(Continued)

(56) References Cited

U.S. PATENT DOCUMENTS 5,050,204 A * 9/1991 Siczek ................ A61B 6/4464
378/197
6,609,826 B1   8/2003 Fujii et al.
(Continued)

FOREIGN PATENT DOCUMENTS

CN   101392491 A   3/2009
CN   102014755 A   4/2011
(Continued)

OTHER PUBLICATIONS

CN202010097620.7 first office action.
PCT/CN2021/074140 international search report and written opinion.

*Primary Examiner* — Irakli Kiknadze
(74) *Attorney, Agent, or Firm* — IPro, PLLC

(57) ABSTRACT

Provided is a C-arm X-ray apparatus, which includes a C-arm translation assembly, a support column, a base, a counterweight, and an adjustment device, wherein one end of the support column is connected to the base, and the other end of the support column is slidably connected to the C-arm translation assembly; the counterweight is slidably connected to the base; and the adjustment device is connected to the counterweight, and configured to drive the counterweight to move by a preset distance in a direction opposite to a first direction in the case that the C-arm translation assembly moves in the first direction, such that a gravity center of the C-arm X-ray apparatus remains at a preset position.

17 Claims, 10 Drawing Sheets

(58) Field of Classification Search
CPC ....... A61B 6/4482; A61B 6/102; A61B 6/105;
A61B 6/586; A61B 6/4452; A61B
6/4233; A61B 6/588; A61B 6/4464; A61B
6/4458; A61B 6/0407; A61B 6/027; A61B
6/4435; A61B 6/504; A61B 6/4283; A61B
6/4291; A61B 6/545; A61B 6/566; A61B
6/587; H05G 1/02
USPC ........................................................ 378/197
See application file for complete search history.

(56) References Cited

U.S. PATENT DOCUMENTS

| | | | | |
|---|---|---|---|---|
| 9,398,675 B2* | 7/2016 | Eaves | ................... | A61B 6/4441 |
| 2008/0122936 A1* | 5/2008 | Lomnes | ............... | A61B 6/4441 |
| | | | | 348/E5.025 |
| 2009/0232282 A1* | 9/2009 | Belson | ................. | A61B 6/4441 |
| | | | | 378/209 |
| 2011/0058644 A1 | 3/2011 | Thran et al. | | |
| 2011/0200176 A1 | 8/2011 | Sharpless | | |
| 2013/0094630 A1 | 4/2013 | Limmer et al. | | |
| 2015/0126863 A1 | 5/2015 | Lee et al. | | |
| 2016/0148398 A1* | 5/2016 | Takemoto | ............... | A61B 6/547 |
| | | | | 378/62 |
| 2019/0099143 A1 | 4/2019 | Liu | | |

FOREIGN PATENT DOCUMENTS

| | | | | |
|---|---|---|---|---|
| CN | 102202577 A | 9/2011 | | |
| CN | 102727225 A | 10/2012 | | |
| CN | 103912218 A | 7/2014 | | |
| CN | 104173069 A | 12/2014 | | |
| CN | 204468110 U | 7/2015 | | |
| CN | 110763707 A | 2/2020 | | |
| CN | 111281407 A | 6/2020 | | |
| EP | 539626 A1 * | 5/1993 | ............ | A61B 6/4283 |
| EP | 658332 A1 * | 6/1995 | ............ | A61B 6/102 |
| JP | 2010158261 A | 7/2010 | | |
| TW | M571727 U | 12/2018 | | |

* cited by examiner

C-ARM X-RAY DEVICE

CROSS-REFERENCE TO RELATED APPLICATION

This application is a US national stage of international application No. PCT/CN2021/074140, filed on Jan. 28, 2021, which claims priority to Chinese Patent Application No. 202010097620.7, filed on Feb. 17, 2020 and entitled "C-ARM X-RAY APPARATUS", the entire contents of which are incorporated herein by reference.

TECHNICAL FIELD

The present disclosure relates to a C-arm X-ray apparatus.

BACKGROUND

In recent years, the applications of C-arm X-ray machines are becoming more widespread and won favors among many doctors due to their good controllability, low amount of radiation, and clear images, and thereby have become one of the necessary devices in an operating room in the $21^{st}$ century.

SUMMARY

According to embodiments of the present disclosure, a C-arm X-ray apparatus is provided. The C-arm X-ray apparatus includes: a C-arm translation assembly, a support column, a base, a counterweight, and an adjustment device, wherein
one end of the support column is connected to the base, and the other end of the support column is slidably connected to the C-arm translation assembly; and
the counterweight is slidably connected to the base; and the adjustment device is connected to the counterweight, and configured to drive the counterweight to move by a preset distance in a direction opposite to a first direction in the case that the C-arm translation assembly moves in the first direction, such that a gravity center of the C-arm X-ray apparatus remains at a preset position.

Exemplarily, the adjustment device includes: a follower, a driver and a pusher, wherein the follower is fixed on a side, facing towards the base, of the C-arm translation assembly; the driver is movably connected to the follower; a pusher is movably connected to the driver; and the driver is configured to transmit a movement distance of the follower to the pusher, and the pusher is configured to push the counterweight to move based on the movement distance.

Exemplarily, the follower is a first piston rod, the driver is a piston cylinder, and the pusher is a second piston rod, wherein
the piston cylinder includes a cylinder block, a partition plate, a first piston and a second piston, wherein the partition plate divides an internal space of the cylinder block into a first chamber and a second chamber; the cylinder block is provided with a first opening in communication with the first chamber and a second opening in communication with the second chamber, the first opening and the second opening being both disposed in a same side surface of the cylinder block, and an end, distal from the first opening, of the first chamber is in communication with an end, distal from the second opening, of the second chamber; the first piston is sealingly and slidably connected to an inner wall of the first chamber, and the second piston is sealingly and slidably connected to an inner wall of the second chamber; an adjustment space is formed between the first piston and the second piston; and the first piston rod and the second piston rod are both disposed along the first direction;
one end of the first piston rod passes through the first opening and is connected to the first piston, and the other end of the first piston rod is fixedly connected to the C-arm translation assembly; and
one end of the second piston rod passes through the second opening and is connected to the second piston, and the other end of the second piston rod is fixedly connected to the counterweight.

Exemplarily, a cross-sectional area of the first chamber along a first plane is greater than a cross-sectional area of the second chamber along the first plane, wherein the first plane is perpendicular to the first direction.

Exemplarily, the follower is a first rack, the driver is a gear assembly, and the pusher is a second rack;
the first rack and the second rack are both disposed along the first direction, and the gear assembly is disposed between the first rack and the second rack;
the first rack is disposed on the side, facing towards the base, of the C-arm translation assembly;
the second rack is disposed on a side, facing towards the C-arm translation assembly, of the base; and
the gear assembly includes a fixed shaft and a rotation wheel, wherein an end of the fixed shaft is fixedly connected to the support column; and the rotation wheel is sleeved on an outer surface of the fixed shaft and is rotatably connected to the fixed shaft, and the rotation wheel is disposed between the first rack and the second rack, and the rotation wheel is in engagement with a side, facing away from the C-arm translation assembly, of the first rack, and the rotation wheel is in engagement with a side, facing away from the base of the second rack.

Exemplarily, the fixed shaft includes a first sub-shaft, a second sub-shaft and a third sub-shaft, and the rotation wheel includes a first sub-wheel, a second sub-wheel and a third sub-wheel, wherein the third sub-wheel includes a first gear and a second gear that are disposed concentrically; one end of the first sub-shaft is connected to the support column, one end of the second sub-shaft is connected to the support column, and one end of the third sub-shaft is connected to the support column; the first sub-wheel is sleeved on an outer surface of the first sub-shaft and is rotatably connected to the first sub-shaft, the second sub-wheel is sleeved on an outer surface of the second sub-shaft and is rotatably connected to the second sub-shaft, and the third sub-shaft is sleeved on an outer surface of the third sub-wheel and is rotatably connected to the third sub-shaft; the first sub-wheel is in engagement with a side, facing away from the C-arm translation assembly, of the first rack; the second sub-wheel is in engagement with the first sub-wheel and the first gear respectively; the second gear is in engagement with a side, facing away from the base, of the second rack; and a diameter of the second gear is greater than a diameter of the first gear.

Exemplarily, the adjustment device includes a detection element, a controller, and a driver assembly, wherein the detection element is electrically connected to the controller that is electrically connected to the driver assembly, and the detection element is configured to detect preset information during a movement of the C-arm translation assembly, and the controller is configured to control the driver assembly to drive the counterweight to move based on the preset information.

Exemplarily, the driver assembly includes a first motor, a driver gear and a third rack, the driver gear is connected to a first rotation shaft of the first motor, the first rotation shaft is perpendicular to the driver gear; the driver gear is in engagement with the third rack; and the third rack is connected to the counterweight.

Exemplarily, the driver assembly includes a second motor and a screw rod, an end of the screw rod is connected to a second rotation shaft of the second motor, the counterweight is sleeved on the screw rod, and the screw rod is threadedly connected to the counterweight.

Exemplarily, the detection element is a distance sensor configured to detect and send a movement distance of the C-arm translation assembly to the controller, the preset information includes the movement distance, and the controller is configured to control the driver assembly to drive the counterweight to move by a preset distance based on the movement distance, such that the gravity center of the C-arm X-ray apparatus remains at the preset position.

Exemplarily, the distance sensor includes at least one of a laser ranging sensor, a guyed displacement sensor, and a grating ranging sensor.

Exemplarily, the detection element is a strain sensor disposed on at least one of a side, proximal to the base, of the C-arm translation assembly and a side surface of the support column, the strain sensor is configured to detect and send a strain value of the C-arm X-ray apparatus to the controller; the preset information includes the strain value; and the controller is configured to control the counterweight to move by a preset distance based on the strain value, such that the gravity center of the C-arm X-ray apparatus remains at the preset position.

Exemplarily, the detection element includes at least one row of weighing sensors, each row of the weighing sensors includes two weighing sensors, is disposed along the first direction, and is configured to detect pressure values as received by the C-arm X-ray apparatus at two places along the first direction and send the pressure values to the controller, and the preset information includes the pressure values,
- a state of the C-arm X-ray apparatus includes a moving state and a balanced state;
- in the case that the C-arm X-ray apparatus is in the balanced state, the two pressure values detected by each row of the weighing sensors are equal;
- in the case that the C-arm X-ray apparatus is in a moving state, the two pressure values detected by each row of the weighing sensors change, and the controller is configured to control the driver assembly to drive the counterweight to move based on changes of the two pressure values detected by each row of the weighing sensors until the two pressure values detected by each row of the weighing sensors are equal again.

Exemplarily, the detection element includes two rows of the weighing sensors; a side of the base facing a placement surface of the C-arm X-ray apparatus is rectangular, and a side of the base facing a first surface is a preset surface that includes a first edge and a second edge disposed along the first direction; the two weighing sensors in one of the two rows of weighing sensors are disposed at two ends of the first edge, and the two weighing sensors in the other of the two rows of weighing sensors are disposed at two ends of the second edge.

Exemplarily, the C-arm X-ray apparatus further includes four casters that are disposed on sides, facing away from the base, of the weighing sensors.

Exemplarily, the base includes a support base and a support member, one end of the support column is connected to the support base, the support member is disposed on a side of the support base proximal to the C-arm translation assembly, and the counterweight is disposed on a side, facing away from the base, of the support member and is slidably connected to the support member.

Exemplarily, a mass of the counterweight is 1/N of a mass of the C-arm translation assembly, and the preset distance is N times the movement distance of the C-arm translation assembly, wherein N>1.

Exemplarily, the first direction is parallel to the placement surface of the C-arm X-ray apparatus

DESCRIPTION OF REFERENCE SIGNS

Figure 1:
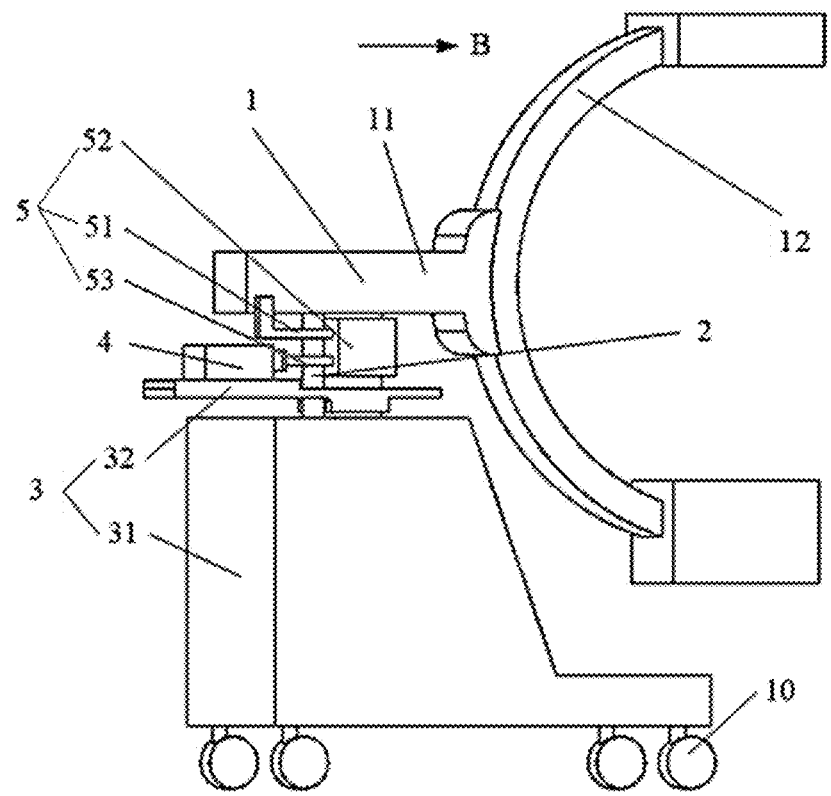
FIG. 1 is a schematic structural diagram of a C-arm X-ray apparatus according to an embodiment of the present disclosure.

1-C-arm translation assembly, 2-support column, 3-base. 31-support base, 32-support member, 4-counterweight, 51-first piston rod, 52-piston cylinder, 521-cylinder block, 522-partition plate, 523-first chamber, 524-second chamber, 525-first opening, 526-second opening, 53-second piston rod, 61-first rack, 62-gear assembly, 621-fixed shaft, 622-rotation wheel, 623-first sub-wheel, 624-second sub-wheel, 625-third sub-wheel, 6251-first gear, 6252-second gear, 63-second rack, 71-first motor, 72-driver gear, 73-third rack, 81-second motor, 82-screw rod, 91-distance sensor, 92-strain sensor, 93-weighing sensor, 10-caster.

DETAILED DESCRIPTION

In order to further explain the technical means and effects as adopted by the present disclosure to achieve the intended purpose of the present disclosure, specific implementations, structures, features, and effects of the C-arm X-ray apparatus proposed in the present disclosure will be described in detail below in combination with the accompanying drawings and preferred embodiments.

The applications of C-arm X-ray machines are becoming more widespread. While designing a C-arm X-ray machine, a center of the whole machine is desired to be positioned exactly in the middle of front and rear casters, such that the whole machine which even has a light weight may still acquire sufficient stability. However, when the C-arm has a translational movement, it may cause changes of the position of a gravity center of the whole machine, which thereby deteriorates stability of the whole machine. Therefore, how to ensure the stability of the whole machine is an urgent problem to be solved by those skilled in the art.

According to an embodiment of the present disclosure, a C-arm X-ray apparatus is provided, which as shown in FIG. 1 to FIG. 12, and includes a C-arm translation assembly 1, a support column 2, a base 3, a counterweight 4 and an adjustment device (not shown in the figures). one end of the support column 2 is connected to the base 3, and the other end of the support column 2 is slidably connected to the C-arm translation assembly 1. The counterweight 4 is slidably connected to the base 3. The adjustment device is connected to the counterweight 4, such that when the C-arm translation assembly 1 moves in a first direction, the adjustment device drives the counterweight 4 to move by a preset distance in a direction opposite to the first direction, such that a gravity center of the C-arm X-ray apparatus remains at a preset position.

Herein, the first direction is parallel to a placement surface of the C-arm X-ray apparatus, and may for example be parallel to the ground.

The C-arm X-ray apparatus provided by the embodiment of the present disclosure includes a counterweight and an adjustment device. In the case that the C-arm translation assembly moves in the first direction, an offset of the gravity center of the C-arm X-ray apparatus may occur, which thereby deteriorates stability of the C-arm X-ray apparatus. In the present disclosure, when the C-arm translation assembly is moved, the adjustment device may adjust the position of the counterweight to make the counterweight move in a direction opposite to the first direction, such that the gravity center of the C-arm X-ray apparatus is back to the preset position, and a good stability of the C-arm X-ray apparatus can still be ensured when the C-arm translation device is moved.

The support column 2 is configured to support the C-arm translation assembly 1 to a first preset height, and an end of the support column 2 is slidably connected with the C-arm translation assembly 1. Exemplarily, a sliding block may be provided at one end of the support column 2 away from the base 3, and a slideway may be provided at a surface of the C-arm translation assembly 1 proximal to the base 3. The sliding block slides along the slideway, such that the support column 2 may be slidably connected to the C-arm translation assembly 1. Furthermore, the C-arm translation assembly 1 includes a moving portion 11 and a C-arm 12. The moving portion 11 has a rectangular parallelepiped shape, an end of the moving portion 11 is connected to the C-arm 12, and the slideway may be disposed on a side, proximal to the base 3, of the moving portion 11. The C-arm translation assembly 1 may move in a horizontal direction, that is in a direction parallel to the ground. An end of the C-arm 12 is provided with an X-ray transmitting end, and the other end is provided with an X-ray receiving end.

The connection between the counterweight 4 and the base 3 is a slidable connection. Exemplarily, a sliding rail may be provided on the base 3; and a sliding portion is provided on the counterweight 4 and slides along the sliding rail, the sliding rail being disposed along a direction same as the moving direction of the C-arm translation assembly 1. The adjustment device is connected to the counterweight 4, and may drive the counterweight 4 to move along a surface of the base 3. When the C-arm translation assembly 1 moves in the first direction, the gravity center may be offset in the first direction. At this point, the adjustment device may adjust the counterweight 4 to move in a direction opposite to the first direction, such that the gravity center can return to the preset position. The C-arm X-ray apparatus has a best stability when the gravity center is at the preset position. The first direction herein is parallel to the ground. Since the support column 2 is telescopic, the horizontal height of the C-arm translation assembly 1 may be controlled by controlling the expansion and contraction of the support column 2, such that the C-arm translation assembly 1 can move up and down. The C-arm translation assembly 1 and the counterweight 4 are disposed respectively on two sides of the preset position.

When the C-arm translation assembly 1 is in the initial position, the gravity center of the C-arm X-ray apparatus is at the preset position; at this point, the stability of the device is the best. When the C-arm translation assembly 1 moves in a direction away from the support column 2, the first direction is namely the direction away from the support column 2; at this point, the counterweight 4 may also move away from the support column 2 in a direction opposite to the moving direction of the C-arm translation assembly 1. After finished using the device, the C-arm translation assembly 1 shall be reset. Thus, the C-arm translation assembly 1 moves in a direction directed to the support column 2, which indicates that the C-arm translation assembly 1 gradually approaches the support column 2. At this point, the first direction is directed to the support column 2 from the C-arm; in the meantime, the counterweight 4 may approach the support column 2 as well, and move in a direction opposite to the moving direction of the C-arm translation assembly 1. Therefore, the first direction in the present disclosure is not limited to one direction, and the moving direction of the C-arm translation assembly can be referred to as the first direction as long as the direction is parallel to the ground.

Exemplarily, the adjustment device includes a follower, a driver and a pusher. The follower is fixed on a side, facing towards the base 3, of the C-arm translation assembly 1, the driver is movably connected to the follower, and the pusher is movably connected to the driver. The driver is configured to transmit a movement distance of the follower to the pusher, and the pusher is configured to push the counterweight 4 to move based on the movement distance. The follower is fixed on the C-arm translation assembly 1, such that the follower can move with the motion of the C-arm translation assembly 1, and the movement distance of the C-arm translation assembly 1 is equal to the movement distance of the follower. The driver may transmit the movement distance of the follower to the pusher, such that the pusher can push the counterweight 4 to move based on the movement distance. The follower, the driver and the pusher in this embodiment are all mechanical structures. The moving direction of the C-arm translation assembly 1 and the moving direction of the counterweight 4 are located on a same straight line.

Figure 2:
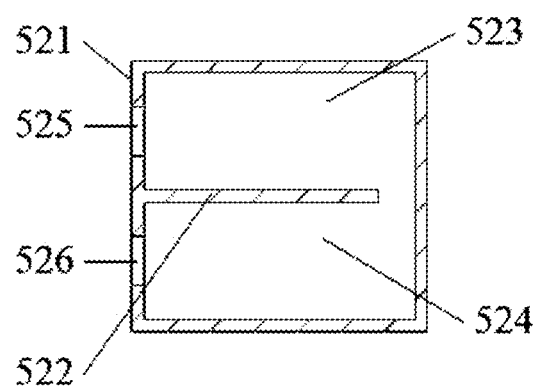
FIG. 2 is another schematic structural diagram of a C-arm X-ray apparatus according to an embodiment of the present disclosure.

Exemplarily, as shown in FIGS. 1 and 2, the follower is a first piston rod 51, the driver is a piston cylinder 52, and the pusher is a second piston rod 53. The piston cylinder 52 includes a cylinder block 521, a partition plate 522, a first piston and a second piston. The partition plate 522 divides an internal space of the cylinder block 521 into a first chamber 523 and a second chamber 524, and the first chamber 523 and the second chamber 524 are not completely separated from each other, but communicate with each other. The cylinder block 521 is provided with a first opening 525 and a second opening 526. The first opening 525 is in communication with the first chamber 523, and the second opening 526 is in communication with the second chamber 524. Moreover, the first opening 525 and the second opening 526 are disposed in a same side surface of the cylinder block 521, and an end, distal from the first opening 525, of the first chamber 523 is in communication with an end, distal from the second opening 526, of the second chamber 524. The first piston is sealingly and slidably connected to an inner wall of the first chamber 523, and the second piston is sealingly and slidably connected to an inner wall of the second chamber 524. An adjustment space is formed between the first piston and the second piston, and the first piston rod 51 and the second piston rod 53 are both disposed along the first direction. In addition, one end of the first piston rod 51 passes through the first opening 525 and is connected to the first piston, and the other end is fixedly connected to the C-arm translation assembly 1; and one end of the second piston rod 53 passes through the second opening 526 and is connected to the second piston, and the other end is fixedly connected to the counterweight 4.

The cylinder block 521 is fixed on a side surface of the support column 2. An end of the first piston rod 51 is connected to a lower surface of the C-arm translation assembly 1; and the lower surface of the C-arm translation assembly 1 is a side, proximal to the base 3, of the C-arm translation assembly 1. The first piston rod 51 may include a first connecting rod and a second connecting rod that are connected to each other. The first connecting rod is perpendicular to the lower surface of the C-arm translation assembly 1. The second connecting rod is disposed along the first direction, an end, distal from the first connecting rod, of the second connecting rod is fixedly connected to the first piston; in addition, the second piston rod 53 is also disposed along the first direction. The shape of the adjustment space formed between the first piston and the second piston may change with the movement of the first piston and the second piston. The adjustment space in the first chamber 523 is referred to as a first space, and the adjustment space in the second chamber 524 is referred to as a second space. The adjustment space is filled with a medium, and the medium may be a liquid or a gas, such as air, which is not limited here. When the C-arm translation assembly 1 moves in a direction away from the support column 2, the direction may be set as a third direction, and as shown in FIG. 1, B refers to the third direction. The first piston rod 51 moves with the C-arm translation assembly 1 in the third direction, and pushes the first piston to move in the first direction, such that the volume of the first space is reduced. Since the first piston and the second piston are both sealingly connected to the inner wall of the cylinder block 521, when the volume of the first space decreases, the pressure of the medium in the first space may increase. In addition, the first piston pushes the medium in the first space to the second space, such that the medium in the second space increases, and thereby the pressure increases. Thus, the second piston is pushed to move in a direction opposite to the third direction. When the first chamber 523 has a same cross section with the second chamber 524, the movement distance of the first piston rod 51 is equal to the movement distance of the second piston rod 53; and in the meantime, it is necessary to ensure that the mass of the counterweight 4 is equal to the mass of the C-arm translation assembly 1 at this point.

As shown in FIG. 2, the first chamber 523 and the second chamber 524 communicate with each other. Exemplarily, a communication port may be provided on the partition plate 522, such that the first chamber 523 and the second chamber 524 can communicate with each other via the communication port. In addition, it is also possible to provide another embodiment, in which the cylinder block 521 is a rectangular parallelepiped, and the partition plate 522 is a rectangle. A length of the partition plate 522 in the first direction is smaller than a length of the cylinder block 521 in the first direction. Three edges of the partition plate 522 are connected to the inner wall of the cylinder block 521, and the other edge of the partition plate 522 is an edge of the partition plate 522 distal from the first opening 525 or the second opening 526 and has a certain width from the inner wall of the of the partition plate 522 have certain widths from the inner wall of the cylinder block 521, such that an opening is formed between the partition plate 522 and the inner wall of the cylinder block 521, thereby allowing the communication between the first chamber 523 and the second chamber 524.

Exemplarily, a cross-sectional area of the first chamber 523 along a first plane is greater than a cross-sectional area of the second chamber 524 along the first plane, wherein the first plane is perpendicular to the first direction. Since the first direction is parallel to the ground, the first plane is perpendicular to the ground. Herein, the first chamber 523 and the second chamber 524 may be disposed along a vertical direction, with the first chamber 523 being on the upper side and the second chamber 524 being on the lower side. In addition, the first chamber 523 and the second chamber 524 may be disposed on a same horizontal plane, such that the first chamber 523 and the second chamber 524 are arranged in parallel. When the cross-sectional area of the first chamber 523 is greater than the cross-sectional area of the second chamber 524, the movement distance of the counterweight 4 may be greater than the movement distance of the C-arm translation assembly 1. Thus, in order to ensure that the gravity center is still at the preset position, the mass of the counterweight 4 may be reduced to be smaller than the mass of the C-arm translation assembly 1. The cross-sectional area of the first cavity 523 along the first plane is S1, and the cross-sectional area of the second cavity 524 along the first plane is S2. When the C-arm translation assembly 1 moves by L1, the corresponding movement distance of the counterweight 4 is L2, satisfying $S1 \times L1 = S2 \times L2$. Thus, when S1 is greater than S2, L2 will be greater than L1. In addition, when the gravity center is at the preset position, the gravity of the C-arm translation assembly 1 is F1, and the gravity of the counterweight 4 is F2, satisfying $F1 \times L1 = F2 \times L2$. Thus, when L1 is smaller than L2, F2 will be smaller than F1, thus the mass of the counterweight 4 may be smaller than the mass of the C-arm translation assembly 1.

In the C-arm X-ray apparatus provided in FIG. 1, the adjustment device is implemented with a piston structure. Whereas, in the C-arm X-ray apparatus provided in FIG. 3, the adjustment device is implemented with a rack-and-gear structure, which will be described in detail below with reference to FIG. 3.

Figure 3:
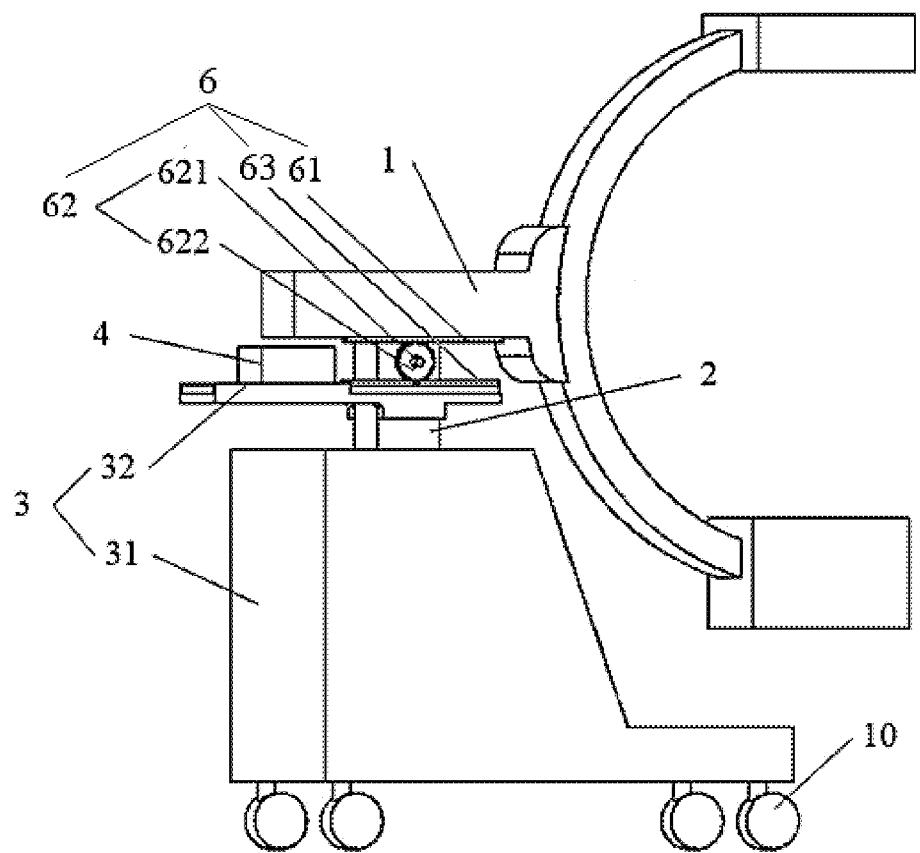
FIG. 3 is still another schematic structural diagram of a C-arm X-ray apparatus according to an embodiment of the present disclosure.

As shown in FIG. 3, the follower is a first rack 61, the driver is a gear assembly 62, and the pusher is a second rack 63. The first rack 61 and the second rack 63 are both disposed along the first direction, and the gear assembly 62 is disposed between the first rack 61 and the second rack 63. The first rack 61 is disposed on a side, facing towards the base 3, of the C-arm translation assembly 1, and the second rack 63 is disposed on a side, facing towards the C-arm translation assembly 1, of the base 3. The gear assembly 62 includes a fixed shaft 621 and a rotation wheel 622. An end of the fixed shaft 621 is fixedly connected to the support column 2; and the rotation wheel 622 is sleeved on an outer surface of the fixed shaft 621, rotatably connected to the fixed shaft 621, and disposed between the first rack 61 and the second rack 63. The rotation wheel 622 is in engagement with a side, facing away from the C-arm translation assembly 1, of the first rack 61, and the rotation wheel 622 also is in engagement with a side, facing away from the base 3, of the second rack 63.

The first rack 61 is fixed on a lower surface of the C-arm translation assembly 1 and can move with the C-arm translation assembly 1. The first rack 61 drivers the rotation wheel 622 of the gear assembly 62 to rotate, and the rotation wheel 622 drives the second rack 63 to move in a direction opposite to the movement of the C-arm translation assembly 1, which thereby drives the counterweight 4 to move in a direction opposite to the movement of the C-arm translation assembly 1. The rotation wheel 622 is sleeved on an outer surface of the fixed shaft 621, and disposed concentrically with the fixed shaft 621, such that the rotation wheel 622 can rotate along the outer surface of the fixed shaft 621. The fixed shaft 621 is fixedly installed on the support column 2, and the fixed shaft 621 is in perpendicular to the support column 2 and parallel to the ground. The counterweight 4 and the C-arm translation assembly 1 are disposed on two sides of the gear assembly 62 respectively. Optionally, the rotation wheel 622 may be connected to a motor. The motor drives the rotation wheel 622 to rotate and thereby drives the counterweight 4 and the C-arm translation assembly 1 to move, rather than moving the C-arm translation assembly 1 manually.

Figure 4:
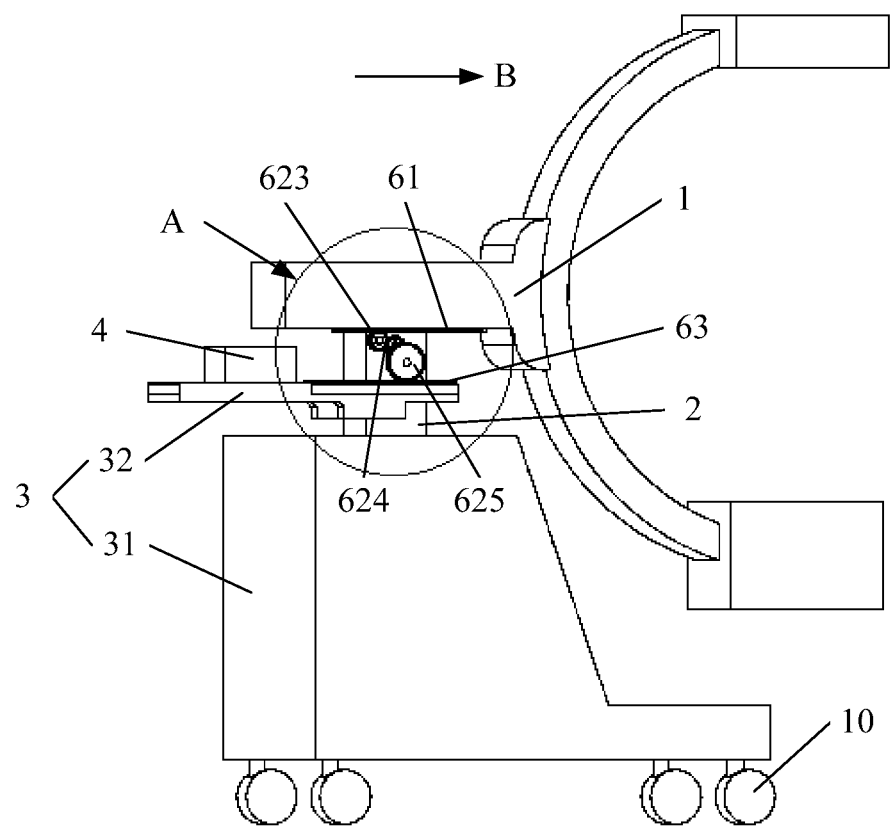
FIG. 4 is yet another schematic structural diagram of a C-arm X-ray apparatus according to an embodiment of the present disclosure.
Figure 5:
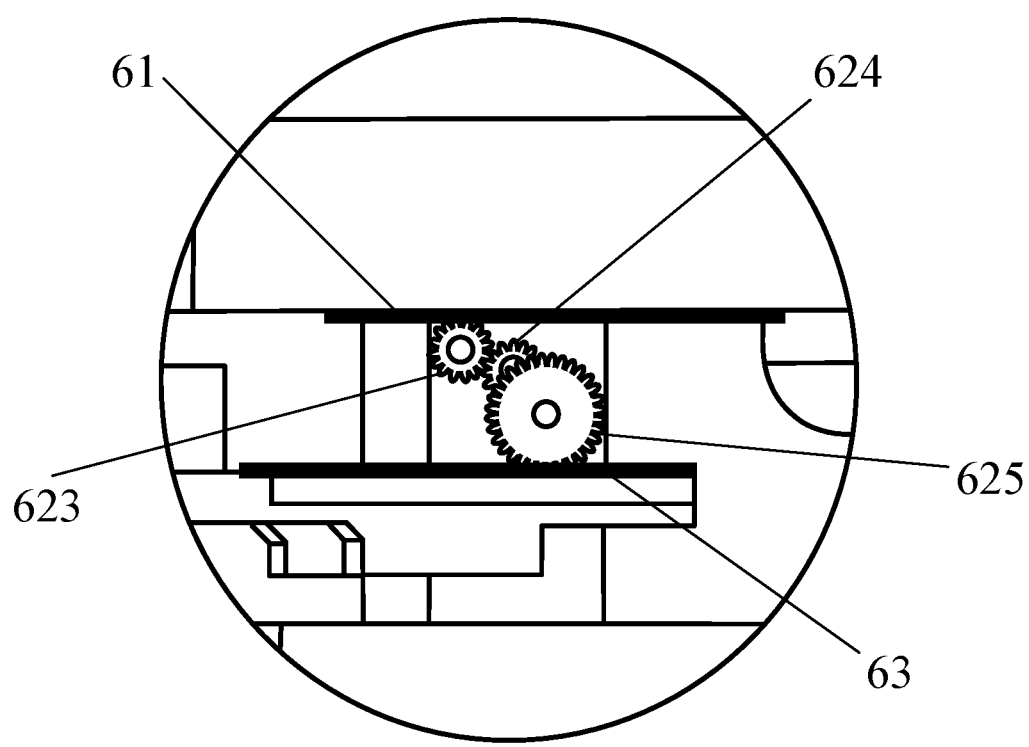
FIG. 5 is an enlarged schematic diagram of a structure at A of a C-arm X-ray apparatus according to an embodiment of the present disclosure.
Figure 6:
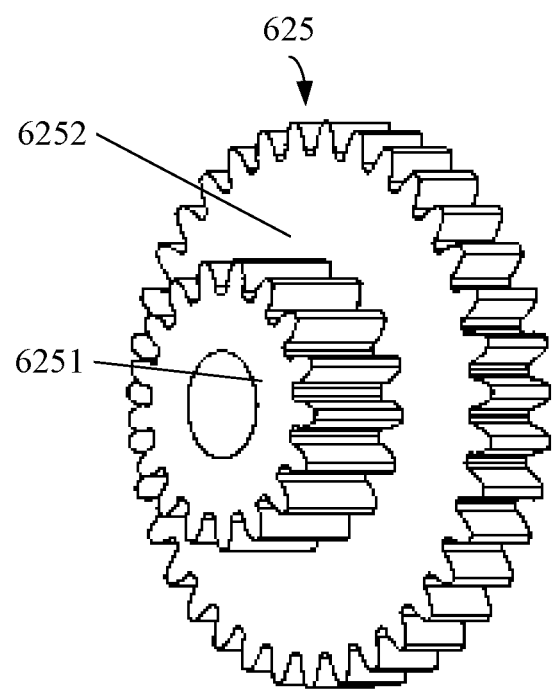
FIG. 6 is another schematic structural diagram of a C-arm X-ray apparatus according to an embodiment of the present disclosure.

Exemplarily, as shown in FIGS. 4, 5 and 6, the fixed shaft 621 includes a first sub-shaft, a second sub-shaft and a third sub-shaft, and the rotation wheel 622 includes a first sub-wheel 623, a second sub-wheel 624, and a third sub-wheel 625. The third sub-wheel 625 includes a first gear 6251 and a second gear 6252. The first gear 6251 is disposed concentrically with the second gear 6252, and is closely attached to a side surface of the second gear 6252. One end of the first sub-shaft is connected to the support column 2, one end of the second sub-shaft is connected to the support column 2, and one end of the third sub-shaft is connected to the support column 2. Furthermore, the three sub-shafts are configured to install the three sub-wheels respectively. The first sub-wheel 623 is sleeved on an outer surface of the first sub-shaft and is rotatably connected to the first sub-shaft; the second sub-wheel 624 is sleeved on an outer surface of the second sub-shaft and is rotatably connected to the second sub-shaft; and the third sub-wheel 625 is sleeved on an outer surface of the third sub-shaft and is rotatably connected to the third sub-shaft. The first sub-wheel 623 is in engagement with a side, facing away from the C-arm translation assembly 1, of the first rack 61; the second sub-wheel 624 is in engagement with the first sub-wheel 623 and the first gear 6251 respectively; and the second gear 6252 is in engagement with a side, facing away from the base 3, of the second rack 63. The diameter of the second gear 6252 is greater than the diameter of the first gear 6251.

The first sub-wheel 623 is disposed concentrically with the first sub-shaft, the second sub-wheel 624 is disposed concentrically with the second sub-shaft, and the third sub-wheel 625 is disposed concentrically with the third sub-shaft. The first rack 61 transmits a movement distance of the C-arm translation assembly 1 to the first sub-wheel 623. When the C-arm translation assembly 1 moves in a direction away from the support column 2 by a movement distance of L, the direction away from the support column 2 may be set as the third direction, and as shown in FIG. 4, B is the third direction. The first rack 61 drives the first sub-wheel 623 to rotate in a fourth direction by a movement distance of L, where the third direction is right along the page, and the fourth direction is counterclockwise. The third sub-wheel 625 drives the second sib-wheel 624 to rotate in a direction opposite to the fourth direction, and the rotating distance of the second sub-wheel 624 is L; whereas the second sub-wheel 624 drives the first gear 6251 to rotate in the fourth direction, and the rotating distance of the first gear 6251 is L. Since the first gear 6251 and the second gear 6252 are both disposed on the third sub-wheel 625, the second gear 6252 also rotates in the fourth direction, but the rotating distance of the second gear 6252 is greater than L, and the distance the the second gear 6252 rotates is set as L3, thus the movement distance of the second rack 63 is equal to L3. Therefore, the movement distance of the second rack 63 is greater than the movement distance of the first rack 61, and the movement distance of the counterweight 4 shall be also greater than the movement distance of the C-arm translation assembly 1, which makes it possible to reduce the weight of the counterweight 4, and further reduce the weight of the whole machine, yet still remain the overall gravity center in the preset position. Optionally, the first sub-wheel may be connected to a motor, and the motor is driven by an electric signal. When the first sub-shaft is driven by the motor, the first rack and the second rack may be driven to move, thereby the movement of the C-arm translation assembly may be electrically controlled.

In the C-arm X-ray apparatus provided in FIGS. 1 to 6, the adjustment devices are implemented by purely mechanical structures. In another embodiment, the adjustment device may further include electrical elements, and the gravity center of the whole machine may be adjusted by detection and control of the electrical elements. This embodiment will be described below in detail.

The adjustment device includes a detection element, a controller, and a driver assembly. The detection element is electrically connected to the controller, and the controller is electrically connected to the driver assembly. The detection element is configured to detect preset information during the movement of the C-arm translation assembly, and the controller is configured to control the driver assembly to drive the counterweight 4 to move based on the preset information.

During the movement of the C-arm translation assembly 1, some parameter values of the C-arm X-ray apparatus may change, and different displacements that the C-arm translation assembly 1 moves correspond to different parameter values. According to the present disclosure, the detection element is provided to detect the parameter value that changes during the movement of the C-arm, and takes the detected parameter value as the preset information, so as to control the movement of the counterweight 4, which thereby ensures that the gravity center of the C-arm X-ray apparatus is at the preset position. The preset information herein may be the movement distance of the C-arm translation assembly 1, or the deformation amount of somewhere on the C-arm X-ray apparatus. After detecting the preset information, the controller controls the driver assembly to work according to the preset information; and the driver assembly drives the counterweight 4 to move to ensure that the gravity center is at the preset position. In addition, it is also possible to provide a feedback element configured to feedback and send a moving displacement of the counterweight to the controller. When the feedback element detects that the counterweight 4 has moved to the preset distance, the driver assembly no longer drives the counterweight 4 to move, Thus the feedback element cooperates with the controller to determine whether the counterweight 4 is driven to move into position.

Figure 7:
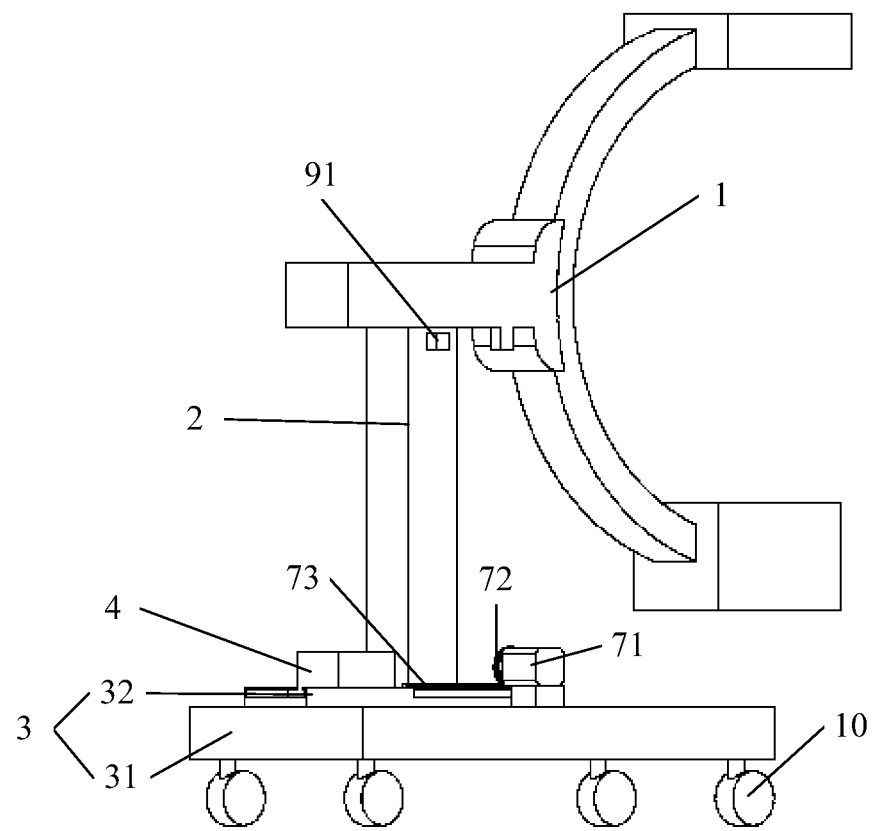
FIG. 7 is still another schematic structural diagram of a C-arm X-ray apparatus according to an embodiment of the present disclosure.
Figure 9:
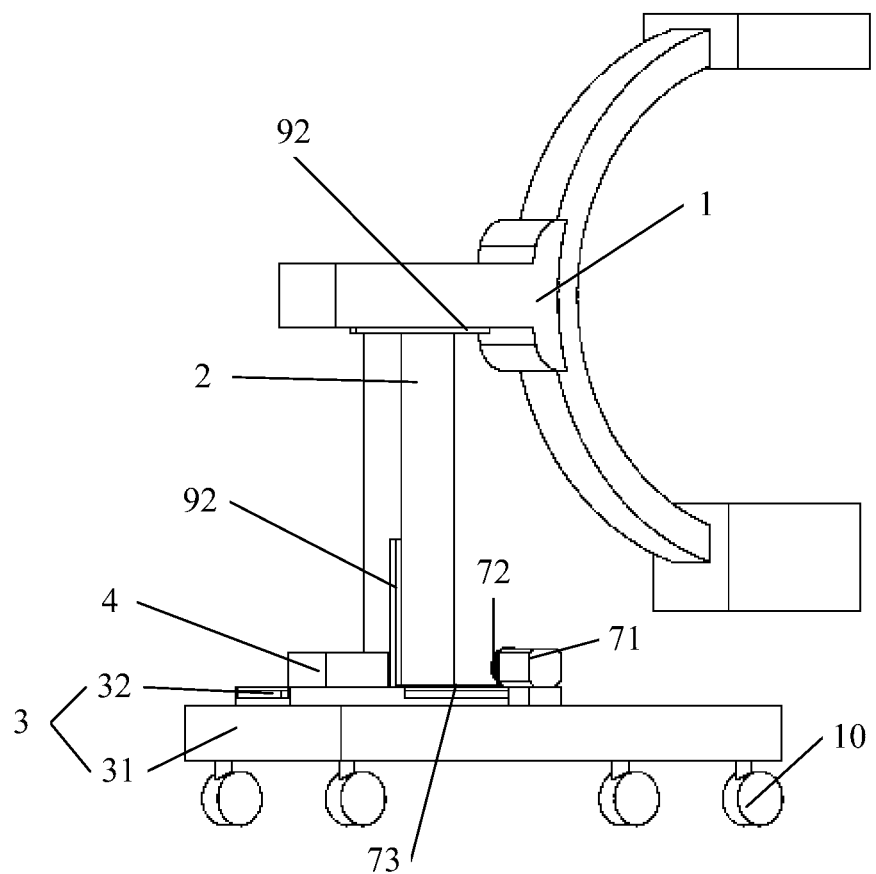
FIG. 9 is another schematic structural diagram of a C-arm X-ray apparatus according to an embodiment of the present disclosure.
Figure 11:
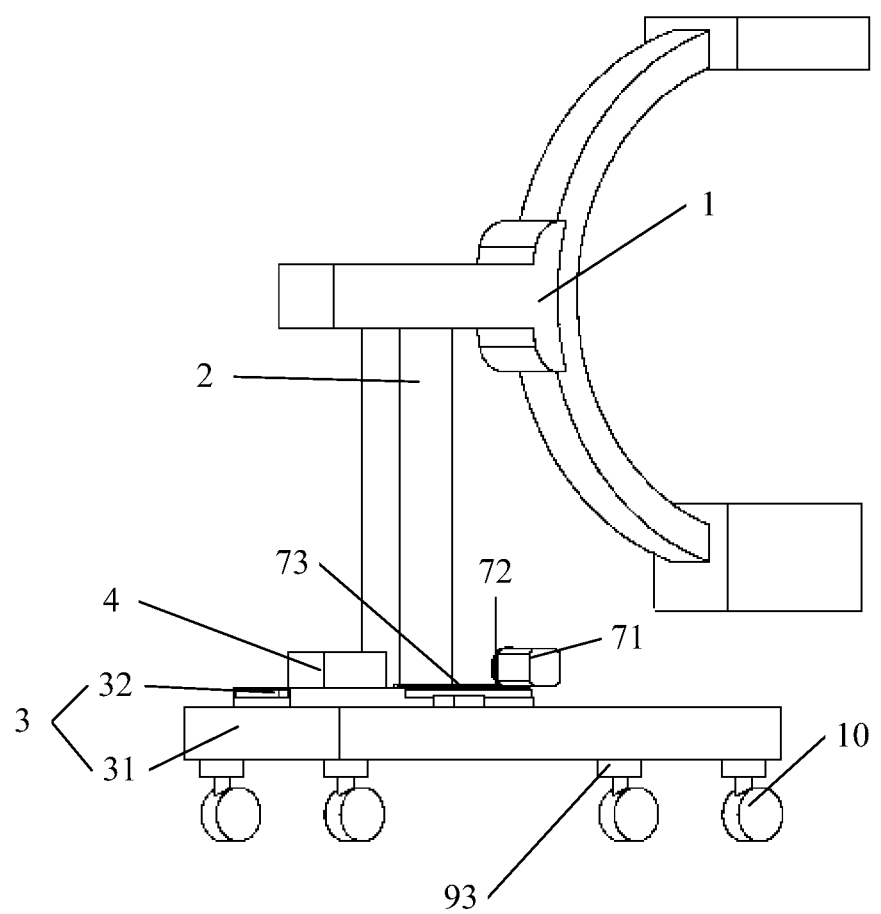
FIG. 11 is yet another schematic structural diagram of a C-arm X-ray apparatus according to an embodiment of the present disclosure.

Exemplarily, as shown in FIGS. 7, 9 and 11, the driver assembly includes a first motor 71, a driver gear 72 and a third rack 73. The driver gear 72 is connected to a first rotation shaft of the first motor 71, and the first rotation shaft is perpendicular to the driver gear 72. The driver gear 72 is in engagement with the third rack 73, and the third rack 73 is connected to the counterweight 4.

The driver assembly includes the first motor 71 serving as a power device. When the first motor 71 works, the first rotation shaft of the first motor 71 rotates. The driver gear 72 is provided on the first rotation shaft to thereby rotate with the rotation of the first rotation shaft. In addition, the rotation of the driver gear 72 may drive the third rack 73 to move; and the rotating direction of the first rotation shaft can determine the moving direction of the third rack 73. The plane where the side surface of the driver gear 72 is disposed may be perpendicular to the ground, and parallel to the first direction.

Figure 8:
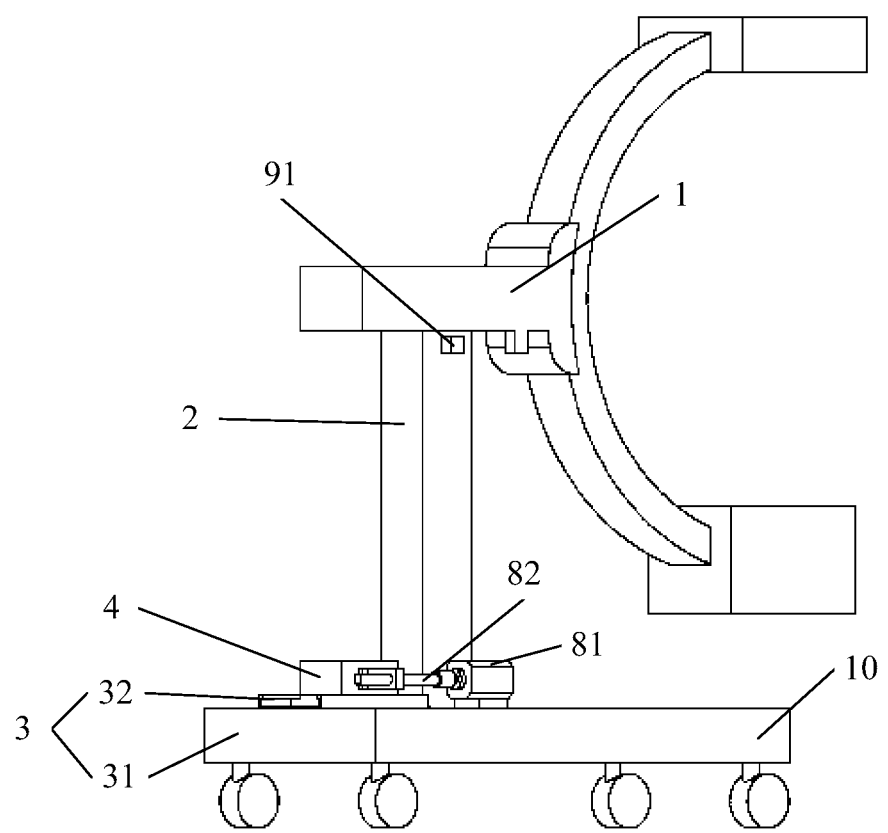
FIG. 8 is yet another schematic structural diagram of a C-arm X-ray apparatus according to an embodiment of the present disclosure.
Figure 10:
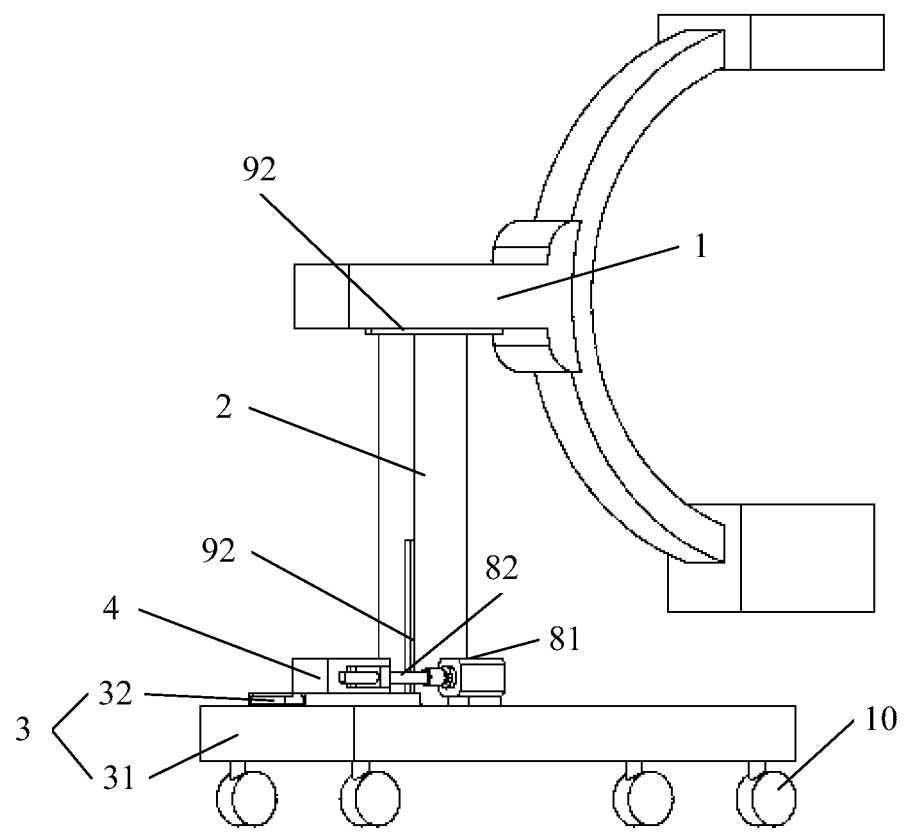
FIG. 10 is still another schematic structural diagram of a C-arm X-ray apparatus according to an embodiment of the present disclosure.
Figure 12:
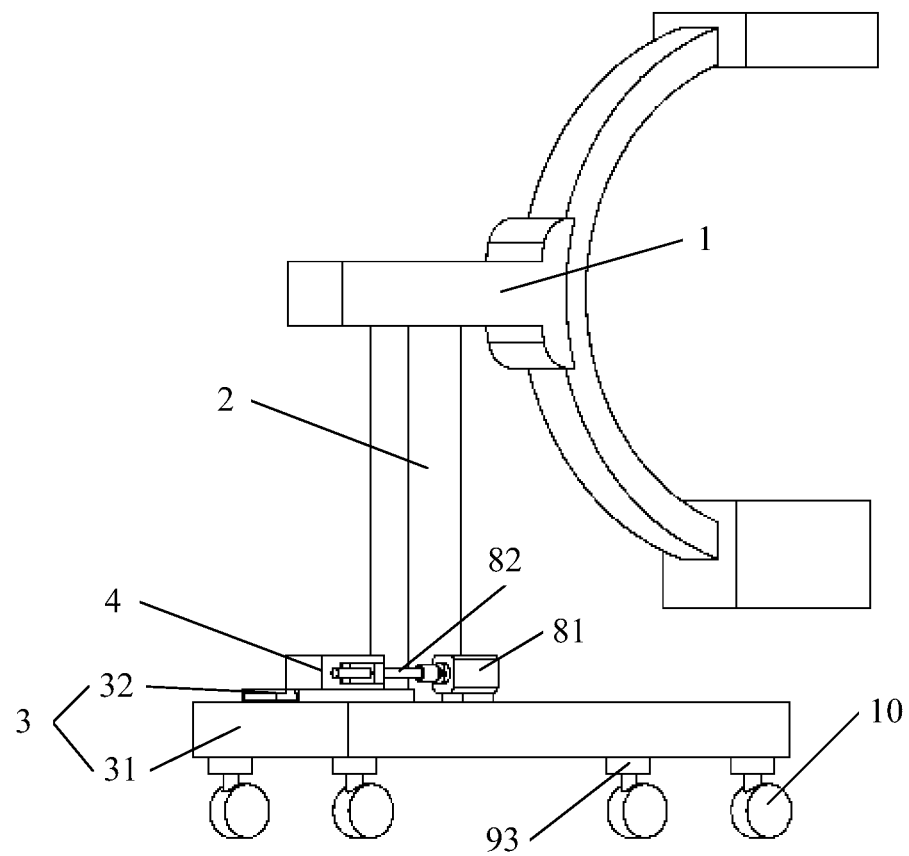
FIG. 12 is another schematic structural diagram of a C-arm X-ray apparatus according to an embodiment of the present disclosure.

Exemplarily, as shown in FIGS. 8, 10 and 12, the driver assembly includes a second motor 81 and a screw rod 82. An end of the screw rod 82 is connected to the second rotation shaft of the second motor 81. The counterweight 4 is sleeved on the screw rod 82, and the screw rod 82 is threadedly connected to the counterweight 4.

The second motor 81 herein may be fixedly disposed on a side, facing towards the C-arm translation assembly 1, of the base 3, and the second rotation shall of the second motor 81 may be connected to the screw rod 82 by a coupling element. The outer surface of the screw rod 82 has threads, and the screw rod 82 is fixedly connected to the second rotation shaft with no relative movement therebetween, which means that the screw rod 82 rotates with the rotation of the second rotation shaft. The counterweight 4 has a moving hole, and the inner surface of the moving hole has threads that mate with the screw rod 82. The moving hole herein may penetrate the entire counterweight 4, or may be a blind hole, and a length of the moving hole determines the moving displacement of the counterweight 4. The screw rod 82 is disposed along the first direction. When the second motor 81 works, the screw rod 82 may rotate accordingly and further push the counterweight 4 to move.

Exemplarily, as shown in FIGS. 7 and 8, the detection element is a distance sensor 91 configured to detect a movement distance of the C-arm translation assembly 1. The preset information includes the movement distance, and the controller is configured to control the driver assembly to drive the counterweight 4 to move by a preset distance based on the movement distance, such that the gravity center of the C-arm X-ray apparatus remains at the preset position.

The preset information may include the movement distance of the C-arm translation assembly 1. The distance sensor 91 detects and sends the movement distance of the C-arm translation assembly 1 to the controller; and the controller controls the counterweight 4 to move. When the mass of the counterweight 4 is equal to the mass of the C-arm translation assembly 1, the driver assembly drives the counterweight 4 to move the same distance as the C-arm translation assembly 1 in the direction opposite to the moving direction of the C-arm translation assembly 1. In this case, the preset distance is equal to the movement distance.

Exemplarily, the distance sensor 91 includes at least one of a laser ranging sensor, a guyed displacement sensor, and a grating ranging sensor. The distance sensor 91 may be disposed on a side surface of the support column 2. While using respective distance sensor 91, it is necessary to install a coupling member to cooperate with the distance sensor. The coupling member is disposed on the C-arm translation assembly 1 and moves with the motion of the C-arm translation assembly 1. When the distance sensor 91 is a guyed displacement sensor, the coupling member is configured to fix the pull string; and when the distance sensor 91 is a laser ranging sensor, the coupling member is configured to reflect laser.

Exemplarily, as shown in FIGS. 9 and 10, the detection element is a strain sensor 92 disposed on a side, proximal to the base 3, of the C-arm translation assembly 1 and/or on a side surface of the support column 2. The strain sensor 92 is configured to detect the strain value of the C-arm X-ray apparatus. The preset information includes the strain value, and the controller is configured to control the counterweight 4 to move a preset based on the strain value, such that the gravity center of the C-arm X-ray apparatus remains at the preset position.

The lower surface of the C-arm translation assembly 1 is slidably connected to the support column 2. During the movement of the C-arm translation assembly 1, the position where the C-arm translation assembly 1 and the support column 2 contact will occur changes, which causes the lower surface of the C-arm translation assembly 1 to undergo a great deformation. In addition, the strain refers to a ratio of the deformation amount to the original size. During the movement of the C-arm translation assembly 1, there will be deformations in many parts of the C-arm X-ray apparatus, thus the strain values in many parts of the C-arm X-ray apparatus may change accordingly. During the movement of the C-arm translation assembly 1, a side surface of the support column 2 and a lower surface of the C-arm translation assembly 1 may both undergo great deformations. In this embodiment, the strain sensor 92 is disposed on the lower surface of the C-arm translation assembly 1 to detect a strain value of the lower surface of the C-arm translation assembly 1, which refers to the first strain value; and the strain sensor 92 is disposed on the side surface of the support column 2 to detect a strain value on the side surface of the support column 2, which refers to the second strain value. It is necessary to determine a correspondence between the first strain value, the second strain value and the movement distance of the C-arm translation assembly 1 through experiments before the movement of the counterweight 4 driven by the controls of the controller. Here is a brief introduction to the experimental process, which includes steps of moving the C-arm translation assembly 1, and recording its movement distance, and meanwhile recording the first strain value and the second strain value corresponding to the movement distance. Then, the steps mentioned above are repeated until acquiring enough data samples. After a lot of experiments, the correspondence between the movement distance of the C-arm translation assembly 1, the first strain value and second strain value may be acquired, Therefore, the movement distance of the C-arm translation assembly 1 may be inferred from the first strain value and/or the second strain value as detected by the strain sensor 92. After detecting the first strain value and/or the second strain value, the strain sensor 92 sends the value to the controller. Then, the controller controls the driver assembly to work, and control the counterweight 4 to move by a preset distance. When the masses of the counterweight 4 and the C-arm translation assembly are equal, the preset distance as moved by the counterweight 4 is equal to the movement distance of the C-arm translation assembly.

Exemplarily, as shown in FIGS. 11 and 12, the detection element includes at least one row of weighing sensors 93, wherein each row of the weighing sensors 93 includes two weighing sensors 93, and the two weighing sensors 93 per row are disposed on two sides of the preset position respectively; and each row of the weighing sensors 93 is disposed along the first direction, and configured to detect pressure values of the C-arm X-ray apparatus at two places along the first direction, and send the pressure values to the controller. The preset information includes the pressure value. The state of C-arm X-ray apparatus includes a moving state and a balanced state. In the case that the C-arm X-ray apparatus is in the balanced state, the two pressure values detected by each row of the weighing sensors 93 are equal. In the case that the C-arm X-ray apparatus is in the moving state, the two pressure values as detected by each row of the weighing sensors 93 change. The controller is configured to control the driver assembly to drive the counterweight 4 to move based on the changes of the two pressure values detected by each row of the weighing sensors 93 until the two pressure values detected by each row of the weighing sensors 93 are equal again. In this embodiment, there is no need to pre-calculate the preset displacement as moved by the counterweight 4, and the preset distance may be reflected by the pressure value detected by the weighing sensors 93. That is, when the two pressure values detected by each row of the weighing sensor 93 are equal again, the moving displacement of the counterweight 4 is namely the preset distance.

In the case that the C-arm X-ray apparatus is in an initial position, the gravity center is at the preset position. In this embodiment, only one row of weighing sensors 93 may be provided; at this time, the number of the weighing sensors 93 is two, which are A and B, respectively. The A and B are respectively disposed on two sides of the preset position, and the three are disposed on a same straight line along the first direction. When the C-arm translation assembly 1 moves in the fourth direction, the C-arm X-ray apparatus is in the moving state, where the fourth direction is directed to B from the preset position. In this case, the pressure value detected by B may increase, Whereas the pressure value detected by A may decrease; thus the controller may determine that the C-arm translation assembly 1 moves in the fourth direction, and then control the driver assembly to drive the counterweight 4 to move in a direction opposite to the fourth direction until the pressure value as detected by A and the pressure value as detected by B are equal again. When multiple rows of weighing sensors 93 are provided, all the changes of the pressure values as detected by each row of the weighing sensors 93 may reflect the moving direction of the C-arm translation assembly 1. When a certain weighing sensor 93 occurs a problem, the controller may acquire the moving direction of the C-arm translation assembly 1 from the weighing sensors 93 in other rows. All the adjustment devices provided by any of the aforesaid embodiments are disposed on a side of the support column 2. It is possible to provide the adjustment devices on the other side of the support column 2. That is, the adjustment devices may be meanwhile provided on both sides of the support column 2.

Exemplarily, the detection element includes two rows of the weighing sensors 93. A side of the base 3 facing the ground is rectangular, and a side of the base facing a first surface is a preset surface that includes a first edge and a second edge both disposed along the first direction. The two weighing sensors in one of the two rows of weighing sensors are disposed at two ends of the first edge, and the two weighing sensors in the other of the two rows of weighing sensors are disposed at two ends of the second edge.

The four weighing sensors 93 are connected in sequence to form a rectangle, which includes a sensor C and a sensor D besides the sensor A and the sensor B described above. The A, B, C, and D are line-connected to form a rectangle. A line where A and B are located is the same as the first direction, and a line where C and D are located is the same as the first direction. Whereas a line where A and C are located is perpendicular to a line where A and B are located, and a line where B and D are located is perpendicular to a line where A and C are located. The moving portion is provided with a rotation shaft inside. An end of the rotation shaft is connected to the C-arm, and the rotation shaft is disposed along the first direction. The C-arm translation assembly 1 may rotate about an axis that is a straight line on which the rotation shaft is disposed. During the rotation, the gravity center of the C-arm X-ray apparatus may be offset in a direction perpendicular to the first direction. In the initial state, the pressure values of A and C are equal, and the pressure values of B and D are equal. After entering the moving state, the pressure values of A and C change, and the pressure values of B and D change. When the gravity center moves towards C, the pressure value of C increases, from which the offset direction of the gravity center may be inferred. Furthermore, an auxiliary counterweight 4 is provided and slidably connected to the base 3, thus the auxiliary counterweight 4 can move in a direction perpendicular to the first direction to match the offset of the counterweight 4 in this direction, so as to remain the gravity center in the preset position.

Exemplarily, the C-arm X-ray apparatus further includes four casters 10 that are disposed on sides, facing away from the base 3, of the weighing sensors 93 respectively. The caster 10 may facilitate the movement of the C-arm X-ray apparatus, and may be a universal wheel or the like, which will not be repeated here.

Exemplarily, the base 3 includes a support base 31 and a support member 32. One end of the support column 2 is connected to the support base 31, and the support member 32 is disposed on a side of the support base 31 proximal to the C-arm translation assembly 1. The counterweight 4 is disposed on a side of the support member 32 away from the base 3 and is slidably connected to the support member 32. The base 3 includes a support base 31 configured to support the whole machine. In order to prevent the counterweight 4 from sliding directly on the support base 31, a support member 32 may be provided and fixed on the support column 2 or on the support base 31, such that the counterweight 4 can slide along a surface of the support member 32 away from the support base 31. Therefore, the effect of the present disclosure can be achieved by only adding the support member 32, the adjustment device, and the like without changing the support base 31 in the prior art. In addition, in order to ensure that the overall weight of the C-arm X-ray apparatus is small, it is possible to reduce the thickness of the support base 31. However, since it also requires to ensure the height of the C-arm translation assembly 1, the support column 2 is configured to have a rather great height and supports the C-arm translation assembly 1 to the first preset height, which thereby causes a rather great distance between the C-arm translation assembly 1 and the base 3. However, by providing the support member 32, a supporting platform may be provided by the support member 32 for the counterweight 4, and the counterweight 4 may be supported to the second preset height by the support member 32, Meanwhile, the adjustment device may be disposed on a side, facing away from the support base 31 of the support member 32; and it is possible to avoid designing the adjustment device too large to occupy a great space. The support column 2 herein is a telescopic device for supporting the C-arm translation assembly 1 to the first preset height.

Exemplarily, a mass of the counterweight 4 is 1/N of a mass of the C-arm translation assembly 1, and the preset distance is N times the movement distance of the C-arm translation assembly, wherein N>1. Herein, the movement distance of the C-arm translation assembly 1 is S, and the moving displacement (i.e., the preset distance) of the counterweight 4 is NS. The weight of the C-arm translation assembly 1 is G, and the weight of the counterweight 4 is G/N, which acquires a balance formula: S×G=NS×G/N. Therefore, in this embodiment, in the case that the position of the gravity center is unchanged, the mass of the counterweight 4 can be reduced by increasing the moving displacement of the counterweight 4 to thereby the weight of the whole machine can be reduced.

Described above are merely specific embodiments of the present disclosure, and the protection scope of the present disclosure is not limited thereto. Within the technical scope of the present disclosure, any variations or substitutions easily envisaged by those skilled in the art shall all fall within the protection scope of the present disclosure. Therefore, the protection scope of the present invention shall be determined by reference to the claims.

What is claimed is:

1. A C-arm X-ray apparatus, comprising:
a C-arm translation assembly, a support column, a base, a counterweight, and an adjustment device, wherein
one end of the support column is connected to the base, and the other end of the support column is slidably connected to the C-arm translation assembly;
the counterweight is slidably connected to the base; and
the adjustment device is connected to the counterweight, and configured to drive the counterweight to move by a preset distance in a direction opposite to a first direction in the case that the C-arm translation assembly moves in the first direction, such that a gravity center of the C-arm X-ray apparatus remains at a preset position; wherein the adjustment device comprises: a follower, a driver and a pusher; wherein the follower is fixed on a side, facing towards the base, of the C-arm translation assembly; the driver is movably connected to the follower; the pusher is movably connected to the driver; and the driver is configured to transmit a movement distance of the follower to the pusher, and the pusher is configured to push the counterweight to move based on the movement distance.

2. The C-arm X-ray apparatus according to claim 1, wherein
the follower is a first piston rod, the driver is a piston cylinder, and the pusher is a second piston rod; wherein
the piston cylinder comprises a cylinder block, a partition plate, a first piston and a second piston, wherein the partition plate divides an internal space of the cylinder block into a first chamber and a second chamber;
the cylinder block is provided with a first opening and a second opening, wherein the first opening is in communication with the first chamber, the second opening is in communication with the second chamber, and the first opening and the second opening are both disposed in a same side surface of the cylinder block, and an end, distal from the first opening, of the first chamber is in communication with an end, distal from the second opening, of the second chamber;
the first piston is sealingly and slidably connected to an inner wall of the first chamber, the second piston is sealingly and slidably connected to an inner wall of the second chamber, an adjustment space is formed between the first piston and the second piston, and the first piston rod and the second piston rod are both disposed along the first direction;
one end of the first piston rod passes through the first opening and is connected to the first piston, and the other end of the first piston rod is fixedly connected to the C-arm translation assembly; and
one end of the second piston rod passes through the second opening and is connected to the second piston, and the other end of the second piston rod is fixedly connected to the counterweight.

3. The C-arm X-ray apparatus according to claim 2, wherein
a cross-sectional area of the first chamber along a first plane is greater than a cross-sectional area of the second chamber along the first plane, wherein the first plane is perpendicular to the first direction.

4. The C-arm X-ray apparatus according to claim 1, wherein
the follower is a first rack, the driver is a gear assembly, and the pusher is a second rack; wherein
the first rack and the second rack are both disposed along the first direction, and the gear assembly is disposed between the first rack and the second rack;
the first rack is disposed on the side, facing towards the base, of the C-arm translation assembly;
the second rack is disposed on a side, facing towards the C-arm translation assembly, of the base, and
the gear assembly comprises a fixed shaft and a rotation wheel, wherein an end of the fixed shaft is fixedly connected to the support column; and the rotation wheel is sleeved on an outer surface of the fixed shaft and is rotatably connected to the fixed shaft, and the rotation wheel is disposed between the first rack and the second rack, the rotation wheel is in engagement with a side, facing away from the C-arm translation assembly, of the first rack, and the rotation wheel is in engagement with a side, facing away from the base, of the second rack.

5. The C-arm X-ray apparatus according to claim 4, wherein
the fixed shaft comprises a first sub-shaft, a second sub-shaft and a third sub-shaft, and the rotation wheel comprises a first sub-wheel, a second sub-wheel and a third sub-wheel, wherein the third sub-wheel comprises a first gear and a second gear that are disposed concentrically; wherein one end of the first sub-shaft is connected to the support column, one end of the second sub-shaft is connected to the support column, and one end of the third sub-shaft is connected to the support column, the first sub-wheel is sleeved on an outer surface of the first sub-shaft and is rotatably connected to the first sub-shaft, the second sub-wheel is sleeved on an outer surface of the second sub-shaft and is rotatably connected to the second sub-shaft; and the third sub-wheel is sleeved on an outer surface of the third sub-shaft and is rotatably connected to the third sub-shaft, and the first sub-wheel is in engagement with a side, facing away from the C-arm translation assembly, of the first rack; the second sub-wheel is in engagement with the first sub-wheel and the first gear respectively; the second gear is in engagement with a side, facing away from the base, of the second rack; and a diameter of the second gear is greater than a diameter of the first gear.

6. The C-arm X-ray apparatus according to claim 1, wherein the adjustment device comprises a detection element, a controller, and a driver assembly; wherein the detection element is electrically connected to the controller, and the controller is electrically connected to the driver assembly, and the detection element is configured to detect preset information during a movement of the C-arm translation assembly, and the controller is configured to control the driver assembly to driver the counterweight to move based on the preset information.

7. The C-arm X-ray apparatus according to claim 6, wherein the driver assembly comprises a first motor, a driver gear and a third rack; wherein the driver gear is connected to a first rotation shaft of the first motor, the first rotation shaft is perpendicular to the driver gear, the driver gear is in engagement with the third rack, and the third rack is connected to the counterweight.

8. The C-arm X-ray apparatus according to claim 6, wherein the driver assembly comprises a second motor and a screw rod, an end of the screw rod is connected to a second rotation shaft of the second motor, the counterweight is sleeved on the screw rod, and the screw rod is threadedly connected to the counterweight.

9. The C-arm X-ray apparatus according to claim 6, wherein the detection element is a distance sensor configured to detect and send a movement distance of the C-arm translation assembly to the controller;

the preset information comprises the movement distance, and the controller is configured to control the driver assembly to drive the counterweight to move by the preset distance based on the movement distance, such that the gravity center of the C-arm X-ray apparatus remains at the preset position.

10. The C-arm X-ray apparatus according to claim 9, wherein the distance sensor comprises at least one of a laser ranging sensor, a guyed displacement sensor, and a grating ranging sensor.

11. The C-arm X-ray apparatus according to claim 6, wherein the detection element is a strain sensor disposed on at least one of a side, proximal to the base, of the C-arm translation assembly, and a side surface of the support column, wherein the strain sensor is configured to detect and send a strain value of the C-arm X-ray apparatus to the controller, the preset information comprises the strain value; and the controller is configured to control the counterweight to move by the preset distance based on the strain value, such that the gravity center of the C-arm X-ray apparatus remains at the preset position.

12. The C-arm X-ray apparatus according to claim 6, wherein the detection element comprises at least one row of weighing sensors, wherein each row of the weighing sensors comprises two weighing sensors, is disposed along the first direction, and is configured to detect pressure values of the C-arm X-ray apparatus at two places along the first direction, and send the pressure values to the controller, and the preset information comprises the pressure values, a state of the C-arm X-ray apparatus comprises a moving state and a balanced state, in the case that the C-arm X-ray apparatus is in the balanced state, the two pressure values detected by each row of the weighing sensors are equal;

in the case that the C-arm X-ray apparatus is in the moving state, the two pressure values detected by each row of the weighing sensors change, and the controller is configured to control the driver assembly to drive the counterweight to move based on changes of the two pressure values detected by each row of the weighing sensors until the two pressure values detected by each row of the weighing sensors are equal again.

13. The C-arm X-ray apparatus according to claim 12, wherein the detection element comprises two rows of the weighing sensors; and a side of the base facing a placement surface of the C-arm X-ray apparatus is rectangular, and a side of the base facing a first surface is a preset surface that comprises a first edge and a second edge both disposed along the first direction; wherein the two weighing sensors in one of the two rows of weighing sensors are disposed at two ends of the first edge; and the two weighing sensors in the other of the two rows of weighing sensors are disposed at two ends of the second edge.

14. The C-arm X-ray apparatus according to claim 13, further comprising: four casters that are disposed on sides, facing away from the base, of the weighing sensors.

15. The C-arm X-ray apparatus according to claim 1, wherein the base comprises a support base and a support member; wherein one end of the support column is connected to the support base, the support member is disposed on a side, proximal to the C-arm translation assembly, of the support base, and the counterweight is disposed on a side, distal from the base, of the support member, and is slidably connected to the support member.

16. The C-arm X-ray apparatus according to claim 1, wherein a mass of the counterweight is 1/N of a mass of the C-arm translation assembly, and the preset distance is N times the movement distance of the C-arm translation assembly, wherein N>1.

17. The C-arm X-ray apparatus according to claim 1, wherein the first direction is parallel to the placement surface of the C-arm X-ray apparatus.

* * * * *